United States Patent
Berglund et al.

(10) Patent No.: US 9,326,870 B2
(45) Date of Patent: May 3, 2016

(54) BIODEGRADABLE STENT HAVING NON-BIODEGRADABLE END PORTIONS AND MECHANISMS FOR INCREASED STENT HOOP STRENGTH

(75) Inventors: Joseph Berglund, Santa Rosa, CA (US); Justin Peterson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 775 days.

(21) Appl. No.: 12/766,480

(22) Filed: Apr. 23, 2010

(65) Prior Publication Data
US 2011/0264186 A1 Oct. 27, 2011

(51) Int. Cl.
| | |
|---|---|
| A61F 2/06 | (2013.01) |
| A61F 2/86 | (2013.01) |
| A61F 2/07 | (2013.01) |
| A61F 2/852 | (2013.01) |
| A61F 2/90 | (2013.01) |
| A61F 2/82 | (2013.01) |
| A61F 2/848 | (2013.01) |

(52) U.S. Cl.
CPC ... *A61F 2/86* (2013.01); *A61F 2/07* (2013.01); *A61F 2/852* (2013.01); *A61F 2/90* (2013.01); *A61F 2002/825* (2013.01); *A61F 2002/8483* (2013.01); *A61F 2210/0004* (2013.01); *A61F 2220/0016* (2013.01); *A61F 2230/0054* (2013.01); *A61F 2250/0031* (2013.01); *A61F 2250/0063* (2013.01)

(58) Field of Classification Search
CPC ............ A61F 2/848; A61F 2002/8483; A61F 2002/8486; A61F 2200/0008; A61F 2200/0016; A61F 2/07; A61F 2/86; A61F 2/82

USPC ........................ 623/1.13–1.16, 1.2, 1.36, 1.38
See application file for complete search history.

(56) References Cited

U.S. PATENT DOCUMENTS

| | | | |
|---|---|---|---|
| 5,817,126 A | 10/1998 | Imran | |
| 5,984,957 A | 11/1999 | Laptewicz et al. | |
| 6,004,347 A * | 12/1999 | McNamara et al. | ........ 623/23.64 |
| 6,123,722 A * | 9/2000 | Fogarty et al. | ................. 623/1.1 |
| 6,945,994 B2 | 9/2005 | Austin et al. | |
| 2002/0002401 A1 | 1/2002 | McGuckin, Jr. et al. | |
| 2002/0123790 A1* | 9/2002 | White | ....................... A61F 2/07 623/1.14 |
| 2003/0120333 A1* | 6/2003 | Ouriel | ....................... A61F 2/07 623/1.14 |
| 2003/0149475 A1* | 8/2003 | Hyodoh et al. | .............. 623/1.19 |
| 2003/0195609 A1 | 10/2003 | Berenstein et al. | |
| 2004/0039415 A1* | 2/2004 | Zamierowski | ................ 606/215 |

(Continued)

FOREIGN PATENT DOCUMENTS

| | | |
|---|---|---|
| EP | 2085050 | 8/2009 |
| WO | WO00/41649 | 7/2000 |

*Primary Examiner* — Katherine Rodjom

(57) ABSTRACT

A hybrid stent prosthesis including a biodegradable tubular body, a first non-biodegradable self-expanding ring coupled to a proximal end of the biodegradable body, and a second non-biodegradable self-expanding ring coupled to a distal end of the biodegradable body. The hybrid stent includes a mechanism for longitudinally compressing the tubular body to increase the radial or hoop strength thereof. The longitudinally compressing mechanism may be protruding elements coupled to and extending radially outward from the hybrid stent or elastomeric compression bands or tethers extending between the non-biodegradable rings. The compression bands may be pre-connected to both non-biodegradable rings prior to stent delivery, or may be connected to one non-biodegradable ring prior to insertion and connected to the other non-biodegradable ring in situ.

15 Claims, 11 Drawing Sheets

(56) References Cited

U.S. PATENT DOCUMENTS

| | | |
|---|---|---|
| 2005/0159803 A1* | 7/2005 | Lad et al. .................. 623/1.13 |
| 2006/0259131 A1* | 11/2006 | Molaei et al. .............. 623/1.44 |
| 2007/0026132 A1 | 2/2007 | Williams et al. |
| 2008/0177380 A1* | 7/2008 | Starksen et al. ........... 623/2.11 |
| 2009/0048664 A1 | 2/2009 | Cage |
| 2009/0234433 A1 | 9/2009 | Richter |
| 2009/0306756 A1 | 12/2009 | Cho et al. |
| 2011/0106115 A1* | 5/2011 | Haselby .............. A61B 5/076 606/151 |

* cited by examiner

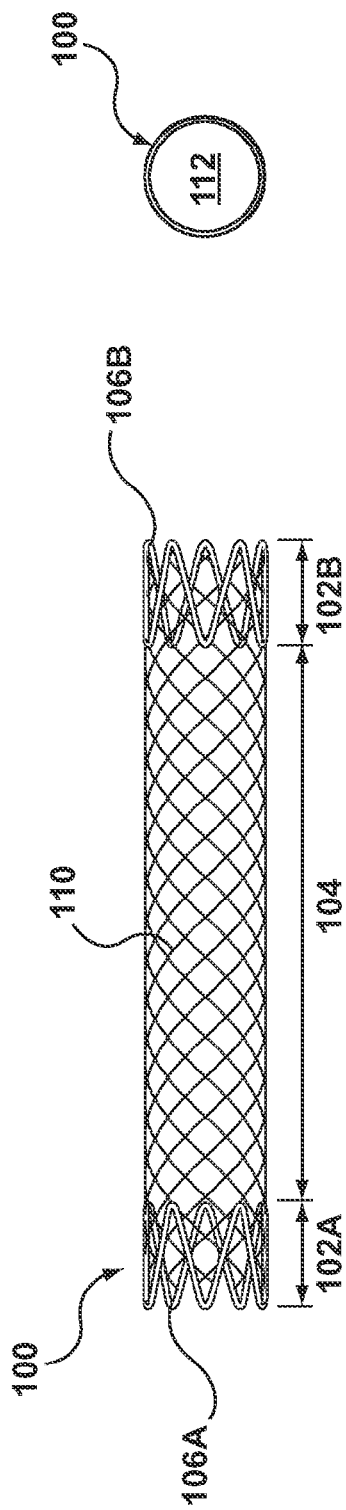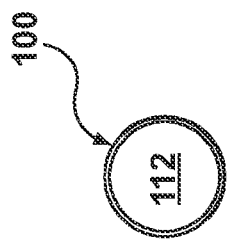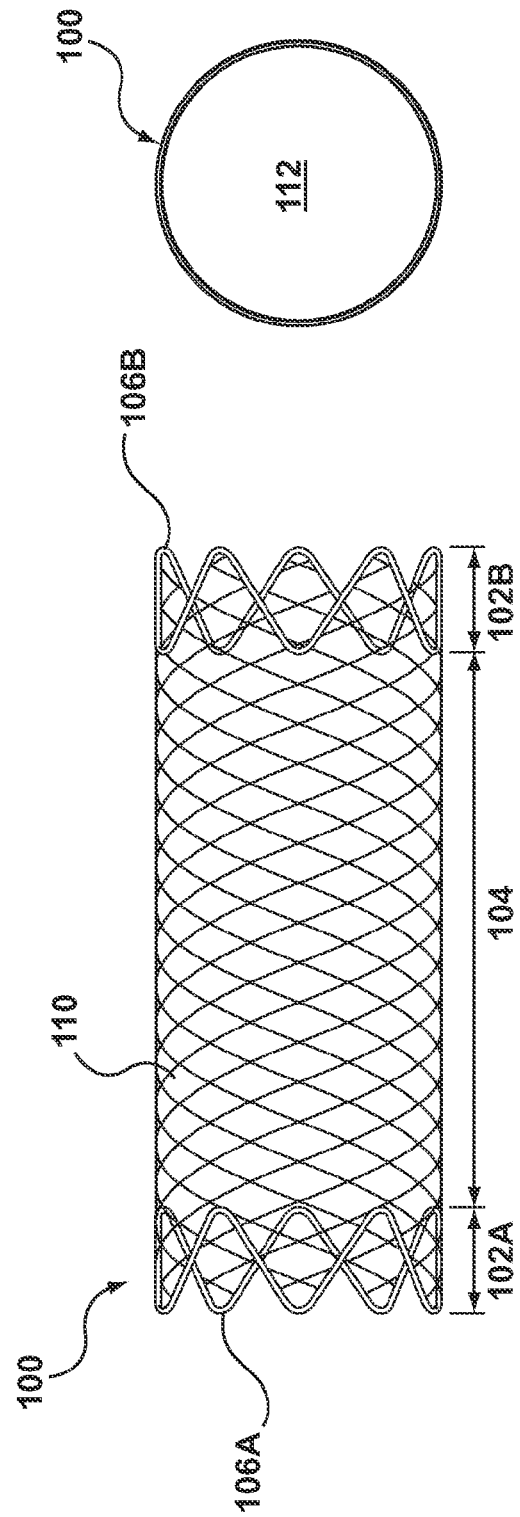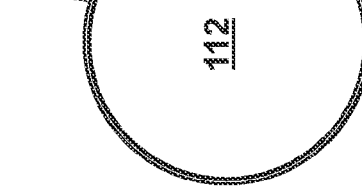

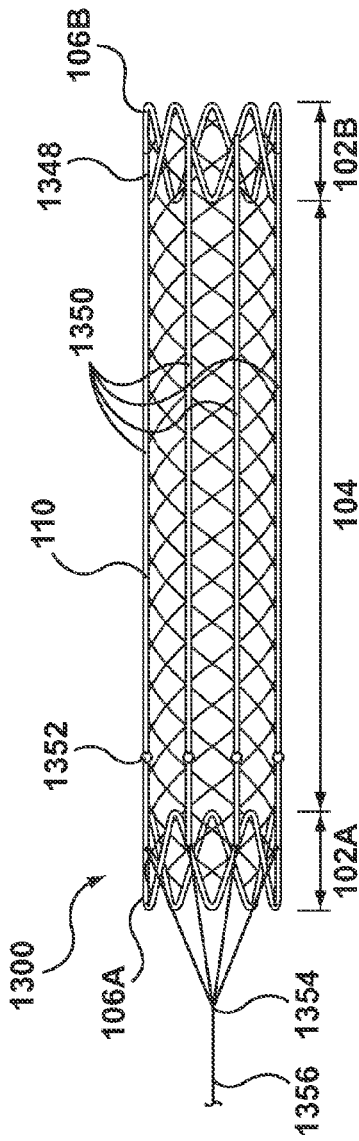
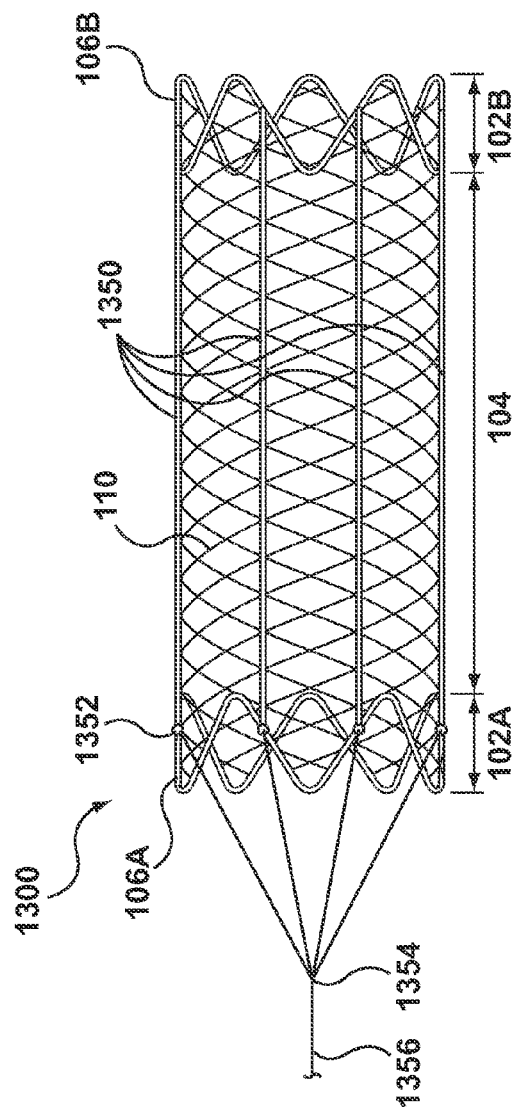

BIODEGRADABLE STENT HAVING NON-BIODEGRADABLE END PORTIONS AND MECHANISMS FOR INCREASED STENT HOOP STRENGTH

FIELD OF THE INVENTION

The invention relates generally to endoluminal prostheses for placement in a body lumen, and more particularly to a stent prosthesis having a biodegradable body.

BACKGROUND OF THE INVENTION

A wide assortment of endoluminal prostheses have been developed, each providing a uniquely beneficial structure to modify the mechanics of a targeted lumen wall within a body lumen. As used herein, "endoluminal prosthesis" is intended to cover a medical device that is adapted for temporary or permanent implantation within a body lumen, including both naturally occurring and artificially made lumens. For example, stent prostheses are known for implantation within body lumens to provide artificial radial support to the wall tissue, which forms the various lumens within the body, and often more specifically, for implantation within the blood vessels of the body. A stent may provide long-term support for damaged or traumatized wall tissues of the lumen or may be implanted, for example, to maintain the patency restored to a blood vessel that was clogged with atherosclerotic plaque. There are numerous conventional applications for stents including cardiovascular, urological, gastrointestinal, and gynecological applications.

Essentially, stents are made to be permanently or temporarily implanted. A permanent stent is designed to be maintained in a body lumen for an indeterminate amount of time and is typically designed to provide long-term support for damaged or traumatized wall tissues of the lumen or to maintain the patency of a vessel clogged with atherosclerotic plaque. A temporary stent is designed to be maintained in a body lumen for a limited period of time in order to maintain the patency of the body lumen, for example, after trauma to a lumen caused by a surgical procedure or an injury or to temporarily open a clogged lumen until natural healing occurs.

Permanent stents, over time, may cause irritation to the surrounding tissue resulting in inflammation at the implant site and restenosis, or re-narrowing of the vessel lumen. Further, if an additional interventional procedure is ever warranted, a previously permanently implanted stent may make it more difficult to perform the subsequent procedure.

Temporary stents, on the other hand, avoid the complications associated with long-term implants. Temporary stents may advantageously be eliminated from body lumens after an appropriate period of time, for example, after the traumatized tissues of the lumen have healed and a stent is no longer needed to maintain the patency of the lumen. Temporary stents may be made from bioabsorbable and/or biodegradable materials that are selected to absorb or degrade in vivo over time. Materials, typically bioabsorbable polymers, and processes typically used to produce bioabsorbable stents result in stents with low tensile strengths and low modulus, compared to metallic stents of similar dimensions. The limitations in mechanical strength of the bioabsorbable stents can result in stent recoil after the stent has been inserted. This can lead to a reduction in luminal area and hence blood flow. In severe cases the vessel may completely re-occlude. In order to prevent the recoil, polymeric stents have been designed with thicker struts (which lead to higher profiles) or as composites to improve mechanical properties. The use of relatively thick struts makes polymeric stents stiffer and decreases their tendency to recoil, but a significant portion of the lumen of the artery can be occupied by the stent. This makes stent delivery more difficult and can cause a reduction in the area of flow through the lumen. A larger strut area also increases the level of injury to the vessel wall and this may lead to higher rates of restenosis i.e. re-occlusion of the vessel. Thus, current totally bioabsorbable stents lack the mechanical properties to sustain vessel lumen size. Even by design manipulation of past bioabsorbable braid configurations and a selection of the best possible known bioabsorbable materials, the totally bioabsorbable stent falls short of current clinically proven products (i.e., metal stents).

It is therefore an object hereof to provide a hybrid stent which has mechanical properties desired in a stent, such as hoop or radial strength, while maintaining at least a mostly bioabsorbable structure. Such a stent provides sufficient support in a body lumen for the duration of a therapeutically appropriate period of time, after which the biodegradable portion then degrades to be eliminated from the patient's body without surgical intervention.

BRIEF SUMMARY OF THE INVENTION

Embodiments hereof relate to a hybrid stent prosthesis including a biodegradable tubular body, a first non-biodegradable self-expanding ring coupled to a proximal end of the biodegradable body, and a second non-biodegradable self-expanding ring coupled to a distal end of the biodegradable body. The hybrid stent includes a mechanism for longitudinally compressing the tubular body and/or maintaining the tubular body in a longitudinally compressed configuration to increase the radial strength of the hybrid stent.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view illustration of an embodiment of a hybrid stent having a biodegradable body and non-biodegradable end portions, wherein the hybrid stent is in a compressed or delivery configuration.

FIG. 2 is an end view of the hybrid stent of FIG. 1.

FIG. 3 is a side view illustration of the hybrid stent of FIG. 1, wherein the hybrid stent is in a radially expanded or deployed configuration.

FIG. 4 is an end view of the hybrid stent of FIG. 1.

FIGS. 13A-13B are side view illustrations of an embodiment of a hybrid stent including longitudinal compression bands that are connected to the stent in situ for increasing the hoop strength of the biodegradable body of the stent.

DETAILED DESCRIPTION OF THE INVENTION

Figure 5:
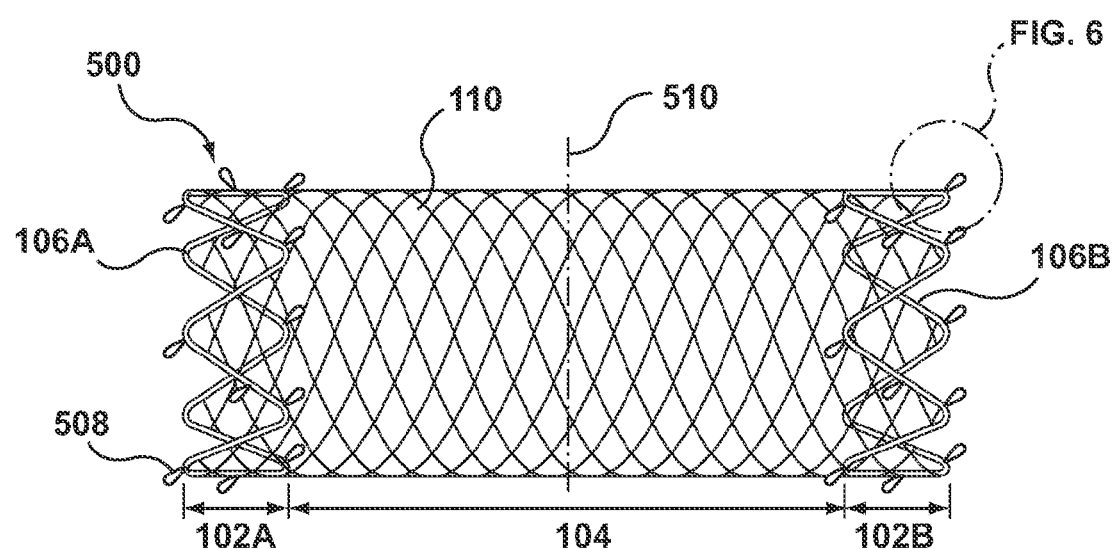
FIG. 5 is a side view illustration of an embodiment of a hybrid stent including barbs on the non-biodegradable end portions for increasing the hoop strength of the biodegradable body of the stent.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. The terms "biodegradable" and "bioabsorbable" are used in the following description with respect to a property of a material. "Biodegradable" is a material that is capable of being decomposed or broken down in vivo and subsequently excreted. "Bioabsorbable" is a material that is capable of being decomposed or broken down in vivo and subsequently resorbed. Both biodegradable and bioabsorbable materials are suitable for purposes of this application and thus for simplicity, unless otherwise directed, biodegradable materials and bioabsorbable materials will collectively be referred to as "biodegradable" herein. In addition, the term "dissolution" as used in the following description is intended to refer to the breakdown of both biodegradable and bioabsorbable materials.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. More particularly, the stents are adapted for deployment at various treatment sites within the patient, and include vascular stents (e.g., coronary vascular stents and peripheral vascular stents such as cerebral stents, superficial femoral artery stents and iliac artery stents), urinary stents (e.g., urethral stents and ureteral stents), biliary stents, tracheal stents, gastrointestinal stents and esophageal stents. Furthermore, there is no intention to be bound by any expressed or implied theory presented in the preceding technical field, background, brief summary or the following detailed description.

Referring now to FIGS. 1-4, a hybrid stent 100 includes a non-biodegradable proximal end portion 102A, a biodegradable midsection or body 104, and a non-biodegradable distal end portion 102B. Biodegradable body 104 degrades in situ as the vessel remodels, leaving only non-biodegradable end portions 102A, 102B within the remodeled vessel. The remodeled vessel then functions as a normal vessel, i.e., with normal vasocontraction and other processes, with an enlarged lumen. FIGS. 1-2 illustrate side and end views, respectively, of hybrid stent 100 in a radially compressed configuration for delivery to the treatment site and FIGS. 3-4 illustrate side and end views, respectively of hybrid stent 100 in a radially expanded or deployed configuration in which hybrid stent 100 comes into contact with the vessel wall. When body 104 is deployed or radially expanded within a vessel, body 104 experiences foreshortening such that the length thereof decreases as the diameter thereof increases. Such foreshortening is illustrated by a comparison between the length of hybrid stent 100 in the radially compressed or delivery configuration of FIG. 1 and the length of hybrid stent 100 in the deployed or radially expanded configuration of FIG. 3.

End portions 102A, 102B include one or more non-biodegradable radially compressible annular or cylindrical rings 106A, 106B, respectively. Rings 106A, 106B are made from a non-biodegradable self-expanding material, such as nickel-titanium alloy (nitinol) or other superelastic metal alloys that bias end portions 102A, 102B of hybrid stent 100 into apposition with an interior wall of a body lumen when released from a restraining mechanism such as a retractable sheath. Rings 106A, 106B may have any suitable configuration including but not limited to a zig-zag or sinusoidal pattern. In one embodiment, rings 106A, 106B may be similar in design to the stent configuration of the Driver® bare metal stent or the Endeavor® drug eluting stent, both of which share the same basic configuration and are available from the assignee of this application, Medtronic Vascular, Inc.

Body 104 of hybrid stent 100 extends between proximal end portion 102A and distal end portion 102B and is a generally hollow tubular or cylindrical structure defining a lumen 112. As shown in FIGS. 2 and 4, the cross-sectional shape of body 104 may be circular. However, the cross-sectional shape may alternatively be ellipsoidal, rectangular, hexagonal rectangular, square, or other polygon. An outer diameter of body 104 may be approximately equal to or slightly larger than an inner diameter of a target body vessel and may be substantially constant along the length thereof. Body 104 is formed by one or more braided, woven, or wound filaments 110. A typical hybrid stent 100 will comprise between 16 and 32 filaments, but more or less filaments may be used. In the embodiment depicted in FIGS. 1 and 3, one set of filaments are in the form of helices which are axially displaced in relation to each other and have the center line of tubular body 104 as a common axis. Another set of filaments are also in the form of helices, which are axially displaced in relation to each other and also have the center line of tubular body 104 as a common axis; however, the second set of helices extend in the opposite direction relative to the first set of helices. The two sets of filaments cross each other at points in the manner shown in FIG. 1. It will be appreciated by one of ordinary skill in the art that the illustrated configuration of body 104 is exemplary and that various configurations may be utilized in accordance herewith. For example, filaments 110 may be employed in a wide variety of filament-based stent configurations, particularly stents that contain coiled and/or braided, knitted, or otherwise woven filaments. Some suitable examples of stent structures are shown in U.S. Pat. No. 5,545, 208 to Wolff et al. and U.S. Published Patent Application Publication No. 2009/0306756 A1 to Cho et al., each of which is incorporated by reference herein in its entirety.

Non-biodegradable end portions 102A, 102B may be attached to biodegradable body 104 in any suitable manner, including bond(s), weld(s), or the like. In one embodiment, a biodegradable suture or polymer band may be tied around each ring 106A, 106B to anchor each ring to the braided filaments 110 of body 104. In another embodiment, a biodegradable adhesive may be utilized to couple end portions 102A, 102B to body 104. Rings 106A, 106B may be coupled to body 104 such that they partially or fully overlap the ends of body 104. Alternatively, rings 106A, 106B may be coupled to body 104 such that they extend proximally and distally, respectively, from the ends of body 104 (not shown).

Body 104 of hybrid stent 100 is formed from a bioabsorbable/biodegradable material that dissolves or breaks down within a vessel. Suitable biodegradable materials include synthetic and naturally derived polymers and co-polymers, as well as blends, composites, and combinations thereof. Examples of suitable materials include but are not limited to polylactide (PLA) [poly-L-lactide (PLLA), poly-DL-lactide (PDLLA)], polyglycolide (PLG or PLGA), polydioxanone, polycaprolactone, polygluconate, polylactic acid-polyethylene oxide copolymers, modified cellulose, collagen, poly(hydroxybutyrate), polyanhydride, polyphosphoester, poly (amino acids), poly(alpha-hydroxy acid) or two or more polymerizable monomers such as trimethylene carbonate, ε-caprolactone, polyethylene glycol, 4-tert-butyl caprolactone, N-acetyl caprolactone, poly(ethylene glycol)bis(carboxymethyl) ether, polylactic acid, polyglycolic acid, or polycaprolactone, fibrin, chitosan, or polysaccharides. In one embodiment hereof, body 104 may be self-expanding due to the inherent resiliency of particular biodegradable materials such as, for example, poly-L-lactide, poly-D-lactide, polyglycolide, such that filaments 110 return to an expanded state when released from a compressed state. Each type of biodegradable polymer has a characteristic degradation rate in the body. Some materials are relatively fast-biodegrading materials (weeks to months) while others are relatively slow-biodegrading materials (months to years). The dissolution rate of filaments 110 may be tailored by controlling the type of biodegradable polymer, the thickness and/or density of the biodegradable polymer, and/or the nature of the biodegradable polymer. In addition, increasing thickness and/or density of a polymeric material will generally slow the dissolution rate of the filaments. Characteristics such as the chemical composition and molecular weight of the biodegradable polymer may also be selected in order to control the dissolution rate of the filaments. In one embodiment, filaments 110 are made from a biodegradable polymer that is degradable within one year and that has adequate mechanical properties to provide wall apposition and strength for at least six months. Anti-fraying technology may optionally be applied to the ends of filaments 110 to prevent unraveling of braided body portion 104.

In an embodiment hereof, at least a portion of body 104 may be coated with a therapeutic agent (not shown) such as a controlled-release polymer and/or drug, as known in the art, for reducing the probability of undesired side effects, e.g., restenosis. The therapeutic agent can be of the type that dissolves plaque material forming the stenosis or can be such as an antineoplastic agent, an antiproliferative agent, an antibiotic, an antithrombogenic agent, an anticoagulant, an antiplatelet agent, an anti-inflammatory agent, combinations of the above, and the like. Such drugs can include zotarolimus, rapamyacin, VEGF, TPA, heparin, urokinase, or sirolimus for example. Of course stent 100 can be used for delivering any suitable medications to the walls of a body vessel.

Non-biodegradable end portions 102A, 102B provide an outward radial force against the vessel in which stent 100 is implanted. Due to this radial force and the fact that end portions 102A, 102B maintain their radial force even as body 104 is degrading over time, end portions 102A, 102B resist longitudinal movement or migration within the vessel. Therefore, the distance between end portions 102A, 102B remains constant, thereby applying and/or maintaining a longitudinal compressive force on body 104 such that body 104 maintains sufficient radial or hoop strength as body 104 degrades over time. Enhanced hoop strength minimizes risk of stent collapse, stent migration, enhances tissue-stent contact which particularly beneficial when hybrid stent 100 includes a therapeutic drug coating, and increases the vessel lumen diameter after stent deployment.

Figure 6:
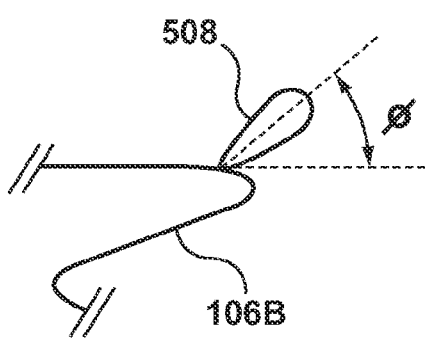
FIG. 6 is an enlarged view of a barb attached to the hybrid stent of FIG. 5.

Referring to FIGS. 5-6, a hybrid stent 500 includes a plurality of protruding elements or barbs 508 extending radially outward from end portions 102A, 102B of stent 500. Barbs 508 permit longitudinal contraction/compression but prevent longitudinal expansion of hybrid stent 500 after deployment, which results in increased radial or hoop strength. More particularly, when hybrid stent 500 is deployed within a vessel, body 104 radially expands and longitudinally contracts. Radial strength is directly related to longitudinal contraction of body 104, and thus the radial strength of stent 500 is increased when body 104 is longitudinally contracted during deployment. However, due to the biodegradable material of body 104, hybrid stent 500 may have a tendency to longitudinally extend after hybrid stent 100 is deployed within a vessel. If hybrid stent 500 longitudinally extends or lengthens, body 104 radially contracts and the hoop strength of hybrid stent 500 decreases. Barbs 508 grip the tissue of the vessel wall and anchor hybrid stent 500 therein to prevent ends 102A, 102B from moving apart from each other, thereby maintaining the hoop strength of longitudinally contracted body 104 after deployment.

As best shown in FIG. 6, each barb 508 is a loop that radially flares at an acute angle from the outer surface of hybrid stent 500 so that when hybrid stent 500 is deployed, barbs 508 protrude into the vessel wall and create an anchor that aids fixing hybrid stent 500 within the vessel. Barbs 508 located on rings 106A, 106B point generally in a direction away from a centerline 510 of hybrid stent 500 after deployment, such that barbs 508 prevent movement of rings 106A, 106B away from each other (i.e., prevent longitudinal extension of hybrid stent 500 after deployment), but permit movement of rings 106A, 106B towards each other (i.e., permit longitudinal contraction of hybrid stent 500 after deployment). Specifically, each barb 508 radially extends from hybrid stent 500 at an angle Ø which is greater than zero degrees but less than ninety degrees to prevent longitudinal extension but permit further longitudinal contraction/compression of hybrid stent 500. As used herein, angle Ø is measured from the outer surface of stent 500 in a clockwise manner when barb 508 is located on first proximal ring 106A or anywhere between first proximal ring 106A and the centerline 510 of stent 500 and angle Ø is measured from the outer surface of stent 500 in a counter-clockwise manner when barb 508 is located on second proximal ring 106B or anywhere between second proximal ring 106B and the centerline 510 of stent 500. In one embodiment, angle Ø is between thirty and sixty degrees. For example, barbs 508 may radially extend from hybrid stent 500 at approximately forty-five degrees. Barbs 508 may also serve as a location or point of connection between biodegradable body 104 and non-biodegradable end portions 102A, 102B.

Barbs 508 may be formed from a non-biodegradable material such as nickel-titanium (nitinol) or other superelastic material that is radially compressible for delivery of hybrid stent 100. In another embodiment, it may be desirable to form barbs 508 from a biodegradable material that is selected to absorb or degrade in vivo over time. Biodegradable materials suitable for barbs 508 include magnesium or a magnesium alloy such as Magnesium AZ31 and Magnesium WE43, other bioabsorbable metals, or bioabsorbable polymers such as polylactic acid, polyglycolic acid, collagen, polycaprolactone, hylauric acid, co-polymers of these materials, as well as composites and combinations thereof.

Figure 7:
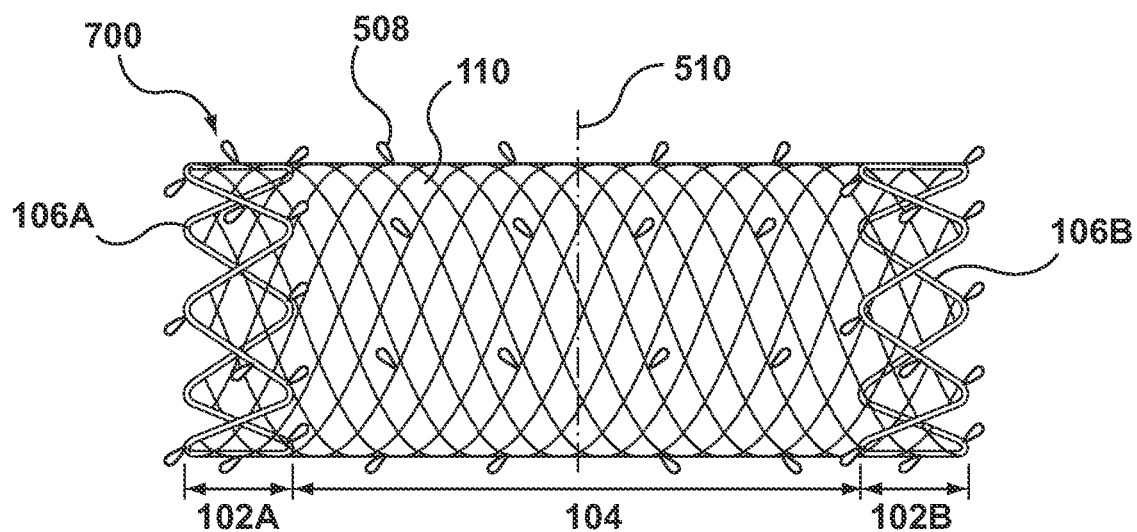
FIG. 7 is a side view illustration of a hybrid stent including barbs in a staggered or random pattern along the length of the stent for increasing the hoop strength thereof.

Although illustrated as extending from end portions 102A, 102B, it should be understood by those of ordinary skill in the art that barbs 508 may be alternatively or additionally attached at any location along the length of hybrid stent 500. For example, FIG. 7 illustrates a plurality of barbs 508 in a "random" or "staggered" pattern along the cylindrical stent body for lodging hybrid stent 700 within the vessel when the stent is expanded.

Figures 8A, 8B:
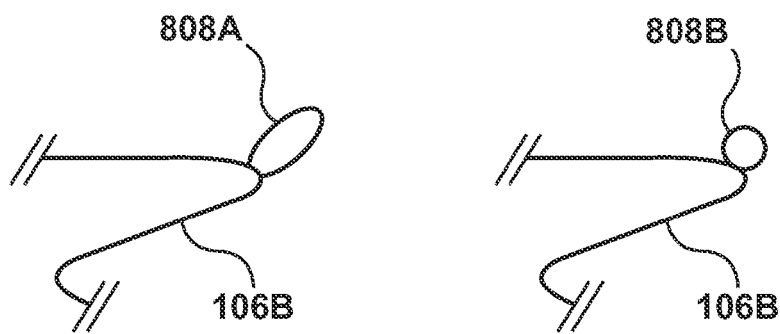
FIGS. 8A-8C illustrate alternative configurations for the barbs of FIG. 5.
Figure 8C:
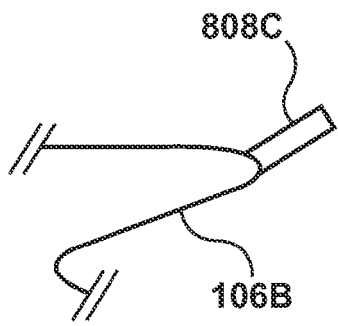

Further, it should be understood by those of ordinary skill in the art that barbs 508 may have any configuration suitable for gripping and lodging within the tissue of the vessel wall. For example, FIG. 8A shows a protrusion element 808A having a flat or planar body that flares or extends radially outwardly from ring 106B so that it protrudes into the vessel wall and creates an anchor that aids fixing the hybrid stent within the vessel. Further, FIG. 8B shows a ball-type protrusion element 808B attached to ring 106B that is operable to lodge into the vessel wall upon stent expansion and create an anchor that aids fixing the hybrid stent within the vessel. FIG. 8C shows a staple-like protrusion element 808C that forms a rectangular arch or loop that flares or extends radially outwardly from ring 106B to protrude into the vessel wall. The configuration of barbs 508 is not limited to the configurations illustrated herein.

Figure 9A:
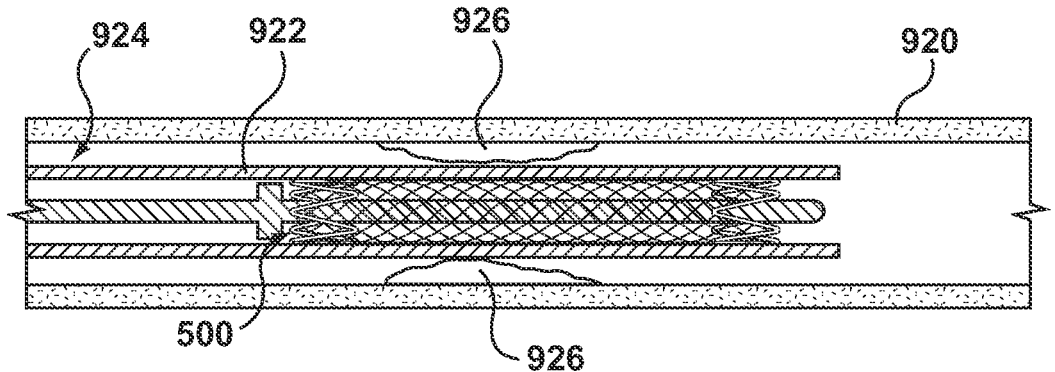
FIGS. 9A-9C illustrate a method of deploying the hybrid stent of FIG. 5 at a treatment site within a vessel, wherein the biodegradable body of the stent is self-expanding.
Figure 9B:
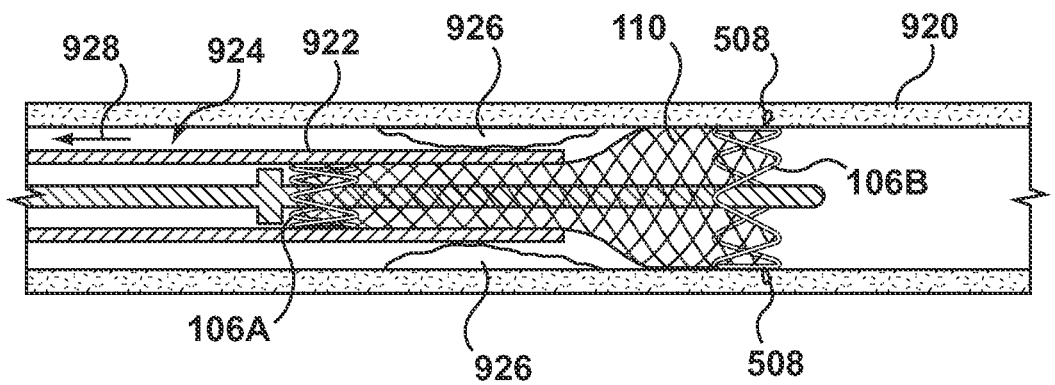
Figure 9C:
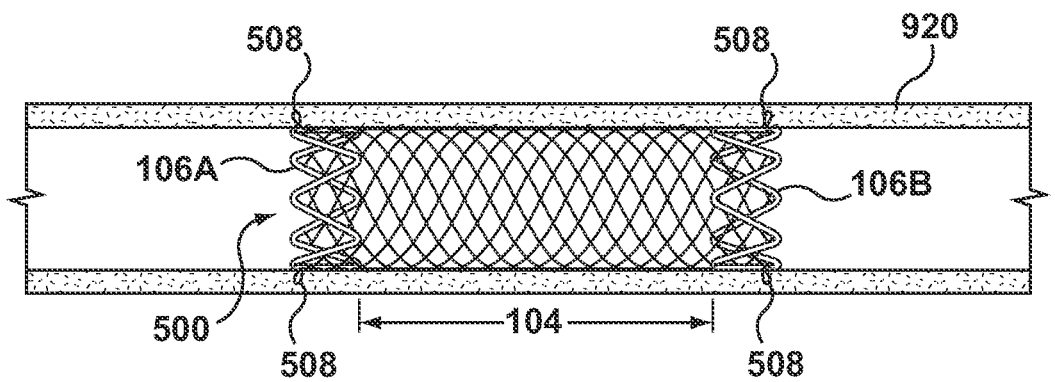

Referring now to FIGS. 9A-9C, a method of deploying hybrid stent 500 having a self-expanding biodegradable body 104 within a vessel 920 is described. Stent deployment can be performed following treatments such as angioplasty, or during initial balloon dilation of the treatment site, which is referred to as primary stenting. As shown in FIG. 9A, a sleeve or sheath 922 is provided to surround and contain hybrid stent 500 in a radially compressed configuration. Deployment of hybrid stent 500 is accomplished by threading a delivery catheter 924 through the vascular system of the patient until hybrid stent 500 is located adjacent to a treatment site, for example, a lesion 926 which may include plaque obstructing the flow of blood through vessel 920.

Once hybrid stent 500 is in position at the treatment site within vessel 920, sheath 922 may be retracted or proximally withdrawn in the direction towards the operator as indicated by directional arrow 928 as shown in FIG. 9B. Since end portions 102A, 102B and body 104 are all formed from a self-expanding material, each portion of hybrid stent 500 radially expands by its own internal restoring forces as sheath 922 is retracted to deploy hybrid stent 500 against the vascular wall of vessel 920 to maintain the opening as is known to one of ordinary skill in the art. Further, barbs 508 will flare or radially extend from hybrid stent 500 as sheath 922 is retracted such that they protrude into the vessel wall. As previously explained, body 104 radially expands and longitudinally contracts as hybrid stent 500 is deployed within a vessel. FIG. 9C illustrates hybrid stent 500 fully deployed within vessel 920. Once implanted, barbs 508 grip the tissue of the vessel wall and, together with rings 106A, 106B, anchor hybrid stent 500 within vessel 920 to prevent undesired longitudinal extension, thereby maintaining the hoop strength of longitudinally contracted body 104 after deployment.

Figure 10A:
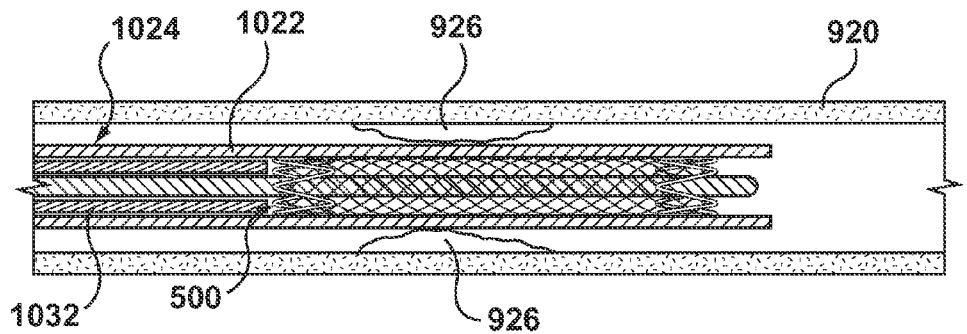
FIGS. 10A-10D illustrate a method of deploying the hybrid stent of FIG. 5 at a treatment site within a vessel, wherein the biodegradable body of the stent is expanded by a compressive force exerted by the operator.
Figure 10B:
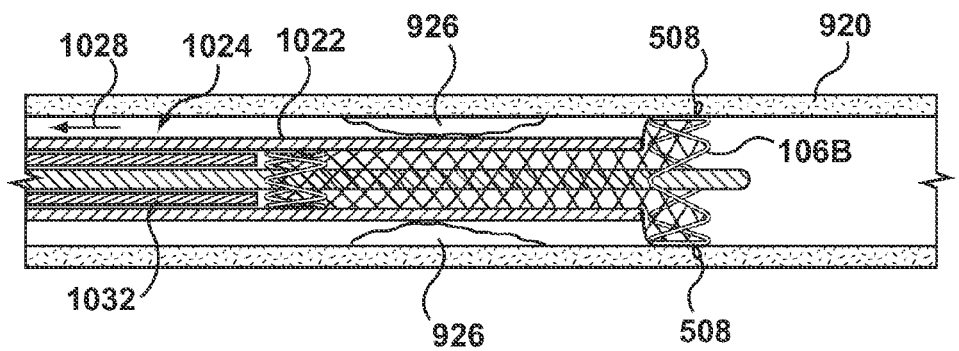

FIGS. 10A-10D illustrate a method of deploying hybrid stent 500 when biodegradable body 104 does not self expand, but may also be used with a body 104 of a stent that does self expand in order to provide increased hoop strength. As shown in FIG. 10A, sheath 1022 surrounds and contains hybrid stent 500 in a compressed, reduced size. Deployment of hybrid stent 500 is accomplished by threading delivery catheter 1024 through the vascular system of the patient until hybrid stent 500 is located adjacent to a treatment site, for example, a lesion 926. Once hybrid stent 500 is in position at the treatment site within vessel 920, sheath 1022 may be retracted or proximally withdrawn in the direction towards the operator as indicated by directional arrow 1028. Ring 106B of end portion 102B will self-expand as shown in FIG. 10B as sheath 1022 is retracted thereover. As ring 106B is deployed against the vascular wall of vessel 920, barbs 508 will flare or radially extend from hybrid stent 500 and protrude into the vessel wall.

Figure 10C:
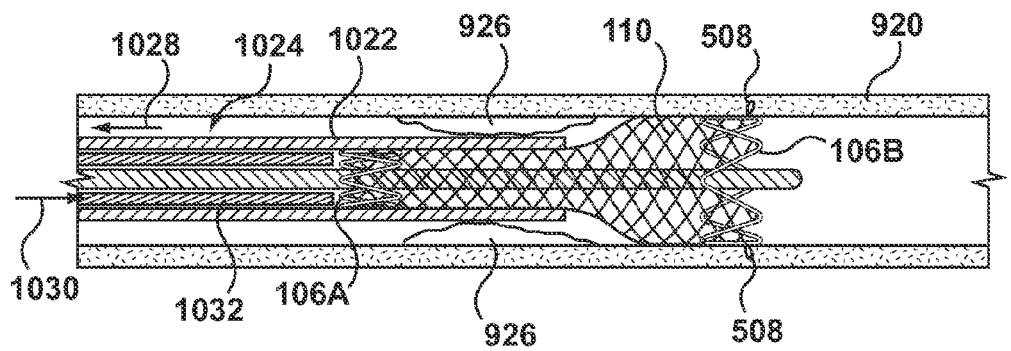
Figure 10D:
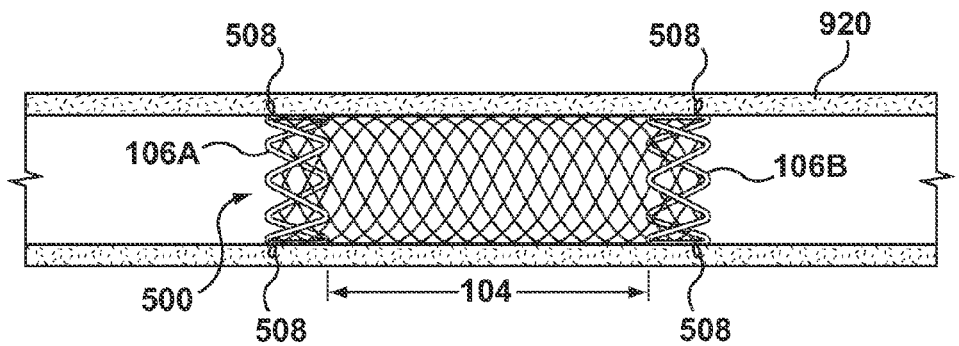

With end portion 102B now anchored against the vascular wall of vessel 920, sheath 1022 is further retracted or proximally withdrawn in the direction towards the operator as indicated by directional arrow 1028 while the operator simultaneously pushes or distally advances a pusher or stopper 1032 in the direction away from the operator as indicated by directional arrow 1030. Pusher 1032 may surround the inner member of delivery catheter 1024 or may be formed as a shoulder (see FIGS. 9A-9B) on the inner member at the proximal end of stent 500. Thus, with ring 106B anchored against the vascular wall, ring 106A is moved closer longitudinally to ring 106B, thereby applying a longitudinal compressive force that radially expands and longitudinally contracts biodegradable body 104 of hybrid stent 500 as shown in FIG. 10C. The longitudinal contraction of body 104 results in increased radial or hoop strength of hybrid stent 500. FIG. 10D illustrates hybrid stent 500 fully deployed within vessel 920. Once implanted, barbs 508 grip the tissue of the vessel wall and anchor hybrid stent 500 within vessel 920 to prevent undesired longitudinal extension, thereby maintaining the increased hoop strength of longitudinally contracted body 104 after deployment.

Figure 11:
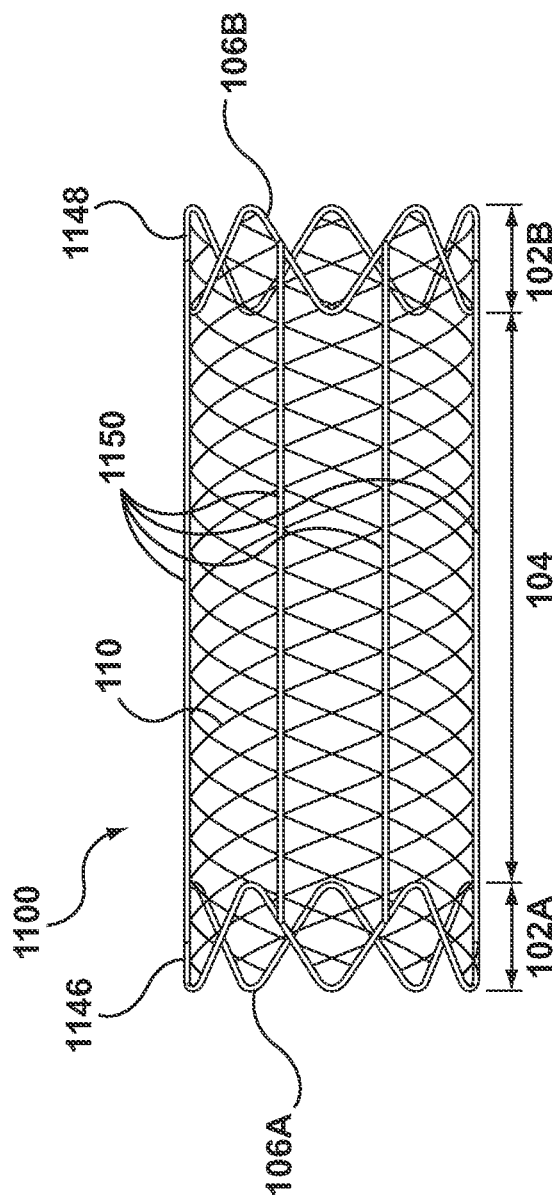
FIG. 11 is a side view illustration of an embodiment of a hybrid stent including pre-connected longitudinal compression bands for increasing the hoop strength of the biodegradable body of the stent.

Referring now to FIG. 11, another mechanism for applying a compressive force on braid 104 in the longitudinal direction in such a way that the hoop or radial strength of the hybrid stent increases is shown. A hybrid biodegradable and non-biodegradable stent 1100 includes one or more pre-connected longitudinal compression bands or tethers 1150 which actively compress the biodegradable body 104 of hybrid stent 1100 to increase the radial strength thereof. More particularly, a first end 1146 of longitudinal compression band 1150 is connected to proximal ring 106A and a second end 1148 of longitudinal compression band 1150 is connected to distal ring 106B. Longitudinal compression bands 1150 extend generally parallel to the longitudinal axis of hybrid stent 1100. Ends 1146, 1148 may be coupled to rings 106A, 106B, respectively, by any suitable mechanical method. In one embodiment, ends 1146, 1148 may be coupled to rings 106A, 106B, respectively, with biodegradable sutures or polymers that are simultaneously connecting end portions 102A, 102B to body 104 of stent 1100. Longitudinal compression bands 1150 may be formed from a biodegradable elastomeric material that essentially pulls or squeezes rings 106A and 106B towards each other, thereby applying a compressive force to biodegradable body 104 and increasing the hoop strength of hybrid stent 1100. Suitable materials for longitudinal compression bands 150 include but are not limited to cross-linked PLG, cross-linked PLA, cross-linked PLGA, or other elastomeric cross-linked bioabsorbable polymers with adequate mechanical properties to longitudinally compress body 104 of hybrid stent 1100.

Figure 12A:
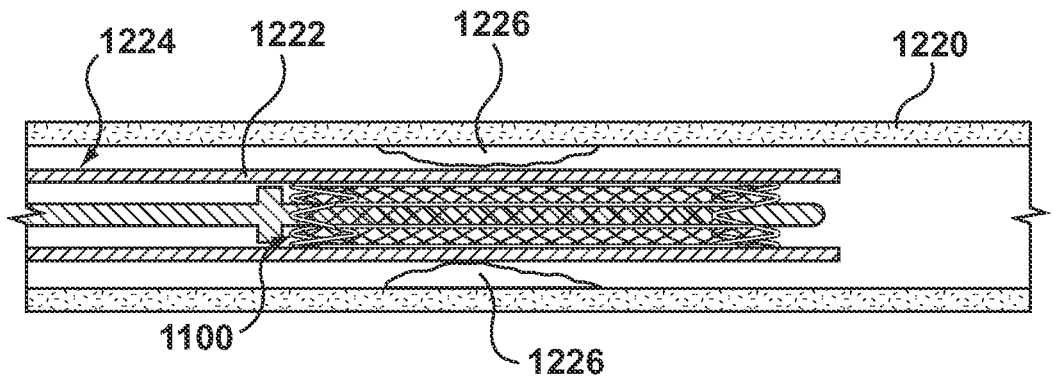
FIGS. 12A-12C illustrate a method of deploying the hybrid stent of FIG. 11 at a treatment site within a vessel.
Figure 12B:
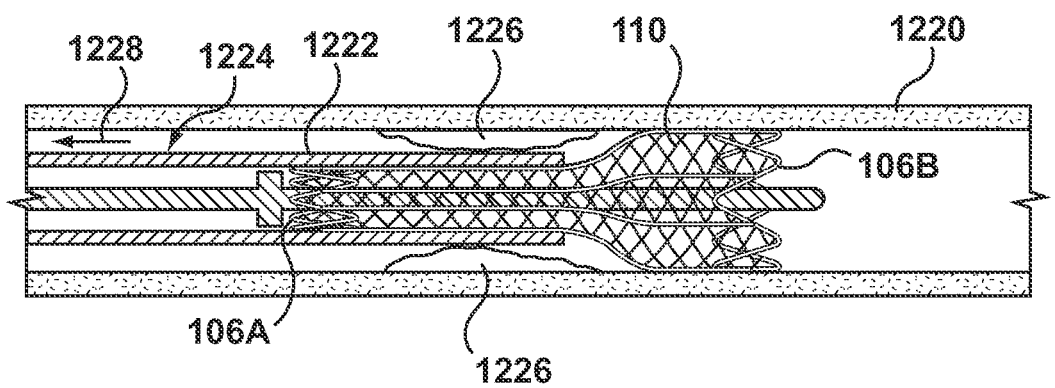
Figure 12C:
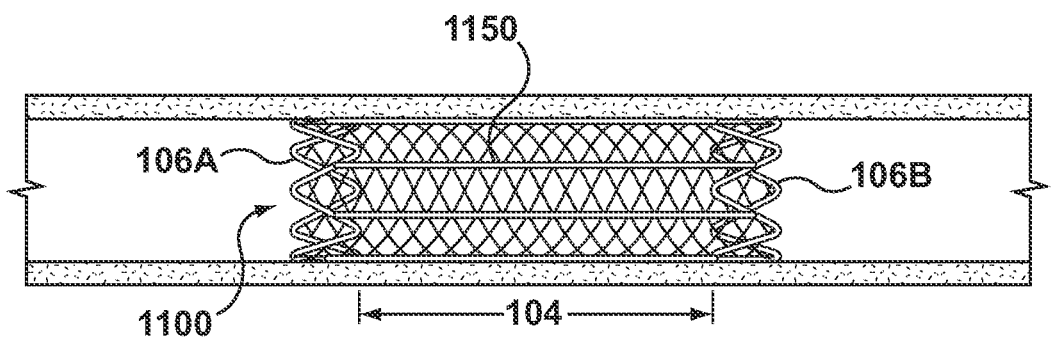

FIGS. 12A-12C illustrate a method of deploying hybrid stent 1100 having longitudinal compression bands 1150 within a vessel 1220. Longitudinal compression bands 1150 are connected to rings 106A, 106B prior to hybrid stent 1100 being loaded into a delivery catheter 1224. Delivery catheter 1224 includes a retractable sleeve or sheath 1222 and may be similar to known delivery catheters for delivery self-expanding stents. As shown in FIG. 12A, sheath 1222 is provided to surround and contain hybrid stent 1100 in a radially compressed configuration. Radially compressing stent 1100 also lengthens it. This radial compression stretches compression bands 1150 longitudinally. Compression bands 1150 thereby store energy and, when released, exert a compression force on stent 1100 to return to their unstretched configuration. Because compression bands 1150 are stored in the stretched configuration within the delivery catheter 1224, the material for compression bands 1150 should be selected to minimize the risk of stress relaxation in longitudinal bands prior to use.

Deployment of hybrid stent 1100 is accomplished by threading a delivery catheter 1224 through the vascular system of the patient until hybrid stent 1100 is located adjacent to a treatment site, for example, a lesion 1226. Once hybrid stent 1100 is in position at the treatment site within vessel 1220, sheath 1222 may be retracted or proximally withdrawn in the direction towards the operator as indicated by directional arrow 1228 in FIG. 12B. End rings 106A, 106B are formed from a self-expanding material such that they radially expand by their own internal restoring forces as sheath 1222 is retracted to deploy end rings 106A, 106B against the vascular wall of vessel 1220. Body 104 may be formed of self-expanding material such that it also self-expands when released from sheath 1222. Alternatively, body 104 may not be formed from a self-expanding material, and stored energy in compression bands 1150 causes body to longitudinally compress as stent 110 is released from sheath 1222.

FIG. 12C illustrates hybrid stent 1100 fully deployed within vessel 1220. Compression bands 1150 assist in radially expanding body 104 by longitudinal compression as stent 1100 exits sheath 1222, thereby increasing hoop strength of body 104. Further, after stent deployment longitudinal compression bands 1150 continue to exert a compression force between 102A, 102B pulling them towards each other to maintain and/or increase the hoop strength of longitudinally contracted body 104.

Figure 14:
FIG. 14 illustrates a portion of a longitudinal compression band of FIG. 13A removed from the hybrid stent.

FIGS. 13A-13B illustrate an embodiment of a hybrid stent 1300 having one or more longitudinal compression bands or tethers 1350 which are connected to hybrid stent 1300 in situ to actively compress the biodegradable body 104 of hybrid stent 1300 to increase the radial strength thereof. Similar to bands 1150, longitudinal compression bands 1350 are formed from a biodegradable elastomeric material that essentially pulls or squeezes rings 106A and 106B towards each other to apply a compressive force to biodegradable body 104 and increase the hoop strength of hybrid stent 1300. Suitable materials for longitudinal compression bands 1350 include but are not limited to cross-linked PLG, cross-linked PLA, cross-linked PLGA, or other elastomeric cross-linked bioabsorbable polymers with adequate mechanical properties to longitudinally compress body 104 of hybrid stent 1300. However, unlike bands 1150, only a distal end 1348 of longitudinal compression bands 1350 is connected to distal ring 106B of hybrid stent prior to implantation, as shown in FIG. 13A. Longitudinal compression bands 1350 include a stop or protrusion 1352 located along the length thereof that becomes seated or lodged within proximal ring 106A after hybrid stent 1300 is deployed at a treatment site within a vessel, as shown in FIG. 13B. In one embodiment, stop 1352 is a knot formed or tied onto band 1350. As best shown in FIG. 14, the length $L_C$ of band 1350 between stop 1352 and distal end 1348 is selected/designed such that band 1350 will apply a longitudinal compressive force to hybrid stent 1300 and increase the radial strength thereof after stop 1352 becomes seated within proximal ring 106A.

Hybrid stent 1300 may include multiple longitudinal compression bands 1350. In one embodiment, the proximal ends of each band 1350 may be joined at a point 1354 and connected to a pull string 1356 that extends through the full length of the delivery system such that when it is desirable to seat stops 1352 into proximal ring 106A, the operator may simply pull on a single pull string 1356 to effectively pull all multiple longitudinal compression bands 1350. In an alternative embodiment (not shown), the proximal end of each longitudinal compression band 1350 may extend through the full length of the delivery system such that the operator may simultaneously or sequentially pull on each longitudinal compression band 1350 to seat stops 1352 into proximal ring 106A.

Figure 15:
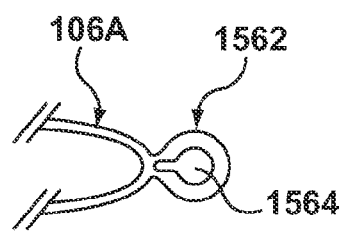
FIG. 15 illustrates a top-view portion of a proximal ring of the hybrid stent of FIG. 13A, the ring including a slot for connecting the longitudinal compression bands to the stent in situ according to an embodiment hereof.
Figure 17A:
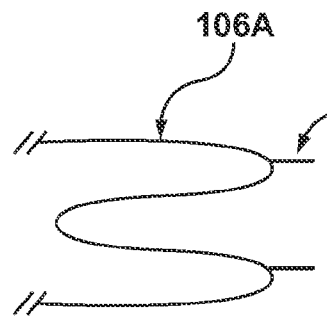
FIGS. 17A-17B illustrate a side-view portion of the proximal ring of either FIG. 15 or FIG. 16.
Figure 17B:
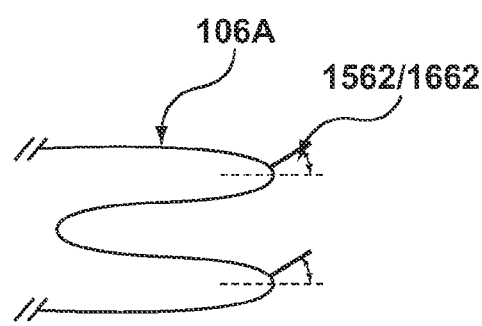

Proximal ring 106A may include a key-hole or slot 1564 sized to receive and contain stop 1352 of longitudinal compression band 1350. As shown in FIG. 15, ring 106A may include an extension 1562 that is attached or integral with ring 106A. Slot 1564 is formed within extension 1562. Extension 1562 may extend generally parallel to the central axis of ring 106A as shown in FIG. 17A or may be inclined with respect to central axis of ring 106A as shown in FIG. 17B such that extension 1562 radially flares at an acute angle from the outer surface of hybrid stent 1300. The incline or angle shown in FIG. 17B may improve the seating of stop 1352 within slot 1564. As will be explained in more detail herein, when it is desirable to seat stop 1352 into proximal ring 106A the operator pulls on longitudinal compression band 1350, optionally via pull string 1356, until stop 1352 "catches" and is lodged within slot 1564.

Figure 16:
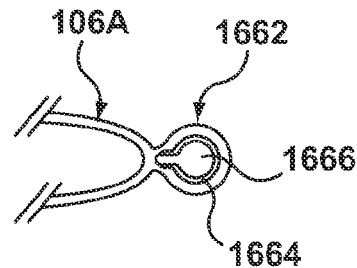
FIG. 16 illustrates a top-view portion of a proximal ring of the hybrid stent of FIG. 13A, the ring including a slot and a flap for connecting the longitudinal compression bands to the stent in situ according to another embodiment hereof.

FIG. 16 illustrates an additional feature that may be utilized for containing stop 1352 of longitudinal compression band 1350 within a slot located on proximal ring 106A of hybrid stent 1300. Similar to FIG. 15, proximal ring 106A includes a key-hole or slot 1664 formed within an extension 1662 that is attached or integral to proximal ring 106A. Extension 1662 may extend generally parallel to the central axis of ring 106A as shown in FIG. 17A or may be inclined with respect to central axis of ring 106A as shown in FIG. 17B such that extension 1662 radially flares at an acute angle from the outer surface of hybrid stent 1300. However, unlike FIG. 15, a trap-door or flap 1666 is attached to proximal ring 106A and extends within slot 1664. Flap 1666 is a flat or planar element that has a shape or contour generally similar to the shape or contour of slot 1664. When it is desirable to seat stop 1352 into proximal ring 106A the operator pulls on longitudinal compression band 1350, optionally via pull string 1356, until stop 1352 is lodged or pinched between flap 1666 and extension 1662.

Figure 18A:
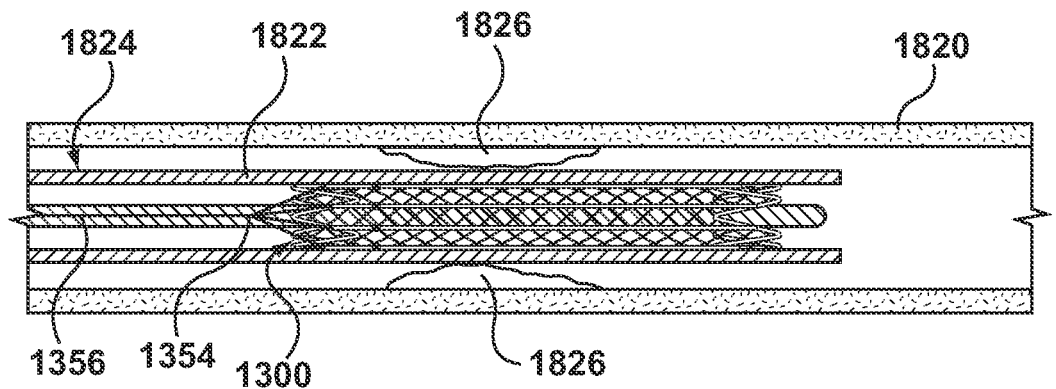
FIGS. 18A-18C illustrate a method of deploying the hybrid stent of FIG. 13A at a treatment site within a vessel and connecting the longitudinal compression bands to the stent in situ, wherein a distal end of the hybrid stent is essentially pulled in situ to connect the bands to the stent, thereby longitudinally compressing the stent and increasing the hoop strength thereof.
Figure 18B:
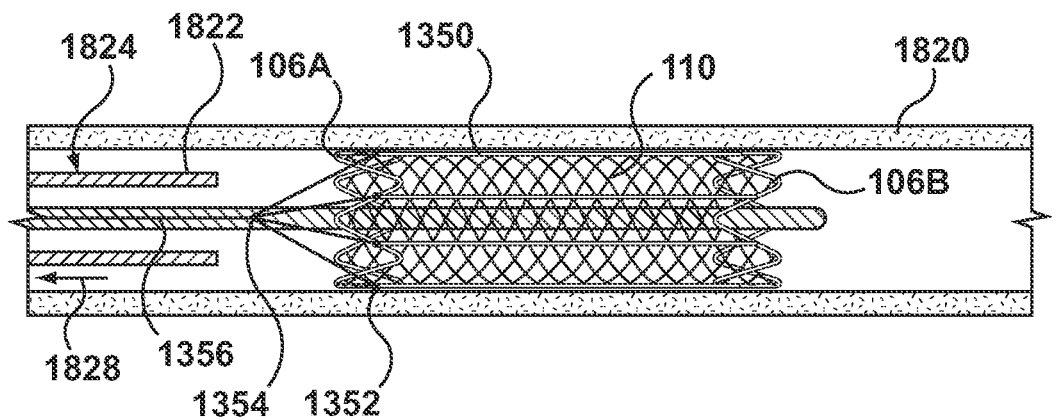
Figure 18C:
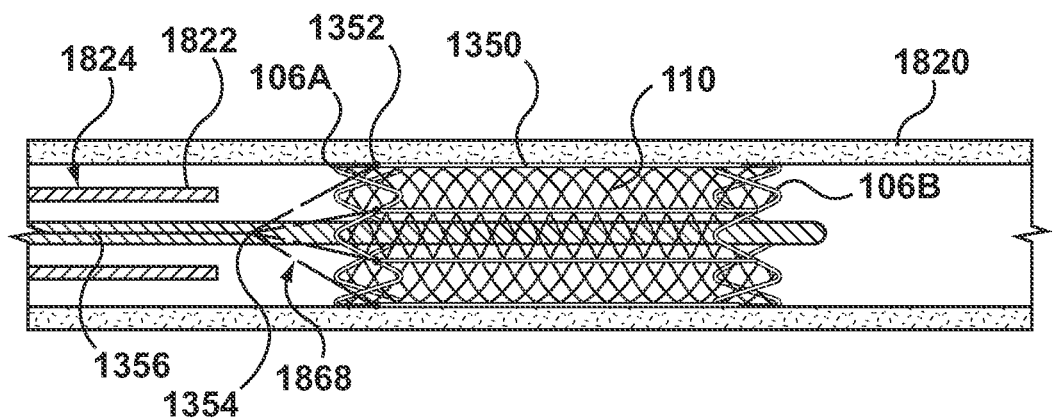

FIGS. 18A-18C illustrate a method of deploying hybrid stent 1300 having longitudinal compression band 1350 within a vessel 1820 and connecting longitudinal compression bands 1850 to stent 1300 in situ. The distal end of longitudinal compression bands 1350 are connected to distal ring 106B of stent 1300 prior to hybrid stent 1300 being loaded into a delivery catheter 1824. Stops 1352 located along the length of longitudinal compression bands 1350 are not yet seated into proximal ring 106A of hybrid stent 1300. Delivery catheter 1824 includes a retractable sleeve or sheath 1822 and may be similar to known delivery catheters for delivering self-expanding stents. As shown in FIG. 18A, sheath 1822 is provided to surround and contain hybrid stent 1300 in a radially compressed configuration. Deployment of hybrid stent 1300 is accomplished by threading a delivery catheter 1824 through the vascular system of the patient until hybrid stent 1300 is located adjacent to a treatment site, for example, a lesion 1826.

Once hybrid stent 1300 is in position at the treatment site within vessel 1820, sheath 1822 may be retracted or proximally withdrawn in the direction towards the operator as indicated by directional arrow 1828 in FIG. 18B. End rings 106A, 106B are formed from a self-expanding material such that they radially expand by their own internal restoring forces as sheath 1822 is retracted to deploy rings 106A, 106B against the vascular wall of vessel 1820. Biodegradable body 104 may also be made from self-expanding material such that it radially expands as it is released from sheath 1822. Alternatively, body 104 may not be formed from a self-expanding material, and the operator may simultaneously apply a compressive force by pulling pull string 1356 as sheath 1822 is retracted or utilizing a pusher as described above. Thus, longitudinal compression bands 1350 may be partially or fully pulled proximally towards the operated as sheath 1822 is retracted. Alternatively, once end portions 102A, 102B and body 104 are all radially expanded or deployed within the vessel, longitudinal compression bands 1350 are pulled in the direction towards the operator as indicated by directional arrow 1828 via pull string 1356 until stops 1352 catch or lodge into proximal ring 106A of hybrid stent 1300 as shown in FIG. 18B. Essentially, the distal end portion 102B of hybrid stent 1300 is essentially pulled in situ to connect bands 1350 to proximal ring 106A of stent 1300, thereby longitudinally compressing the stent and increasing the hoop strength thereof. Mechanisms for connecting bands 1350 to stent 1300 in situ include but are not limited to lodging stops 1352 into a slot as described with respect to FIG. 15 or pinching stops 1352 between a slot and a flap as described with respect to FIG. 16. With longitudinal compression bands 1350 coupled to hybrid stent 1300, longitudinal compression bands 1350 continue to exert a compression force on ends 102A, 102B towards each other and maintain and/or increase the hoop strength of longitudinally contracted body 104.

Additionally, it is noted that the location of stop 1352 on longitudinal compression band 1350 and the amount of pulling performed by the user may determine the final radial diameter and final length of deployed hybrid stent 1300. Specifically, if a particular application requires a greater or lesser deployed diameter for hybrid stent 1300, the length $L_C$ of longitudinal compression band 1300 may be varied by adjusting the location of stop 1352 on longitudinal compression band 1350 and the amount of pulling performed by the user to achieve the desired deployed stent dimensions.

FIG. 18C illustrates hybrid stent 1300 fully deployed within vessel 1820, with longitudinal compression bands 1350 now coupled to both proximal and distal rings 106A, 106B of stent 1300. Longitudinal compression bands 1850 are now cut or otherwise broken apart as indicated by the gap shown at 1868 such that delivery catheter 1824 and pull string 1356 may be proximally retracted and withdrawn from the patient. In one embodiment, delivery catheter 1824 may include an integral cutting element for disengaging longitudinal compression bands 1350 from pull string 1356. In another embodiment, a separate cutting element may be delivered for disengaging longitudinal compression bands 1350 from pull string 1356. As will be apparent to those of ordinary skill in the art, other disengaging mechanisms may be utilized as well, such as for example utilizing an energy source to break apart longitudinal compression bands 1850 or forming weakened areas within longitudinal compression bands 1850 that break apart upon application of a sufficient pulling force by the user after stops 1352 are lodged within proximal ring 106A. After disengagement occurs, hybrid stent 1300 having longitudinal compression bands 1350 attached thereto for increased hoop strength may remain in situ.

Figure 19A:
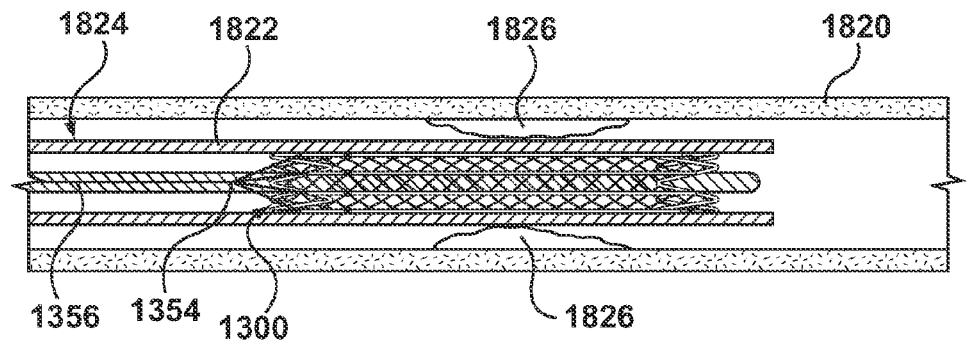
FIGS. 19A-19D illustrate a method of deploying the hybrid stent of FIG. 13A at a treatment site within a vessel and connecting the longitudinal compression bands to the stent in situ, wherein a proximal end of the hybrid stent is essentially pushed in situ to connect the bands to the stent, thereby longitudinally compressing the stent and increasing the hoop strength thereof.

FIGS. 19A-19D illustrate an alternative method of deploying hybrid stent 1300 having longitudinal compression band 1350 within a vessel 1820 and connecting longitudinal compression bands 1850 to stent 1300 in situ. As explained above with respect to FIG. 18A, the distal end of longitudinal compression bands 1350 are connected to distal ring 106B of stent 1300 prior to hybrid stent 1300 being loaded into a delivery catheter 1824. Stops 1352 located along the length of longitudinal compression bands 1350 are not yet seated into proximal ring 106A of hybrid stent 1300. As shown in FIG. 19A, deployment of hybrid stent 1300 is accomplished by threading a delivery catheter 1824 through the vascular system of the patient until hybrid stent 1300 is located adjacent to a treatment site, for example, a lesion 1826.

Figure 19B:
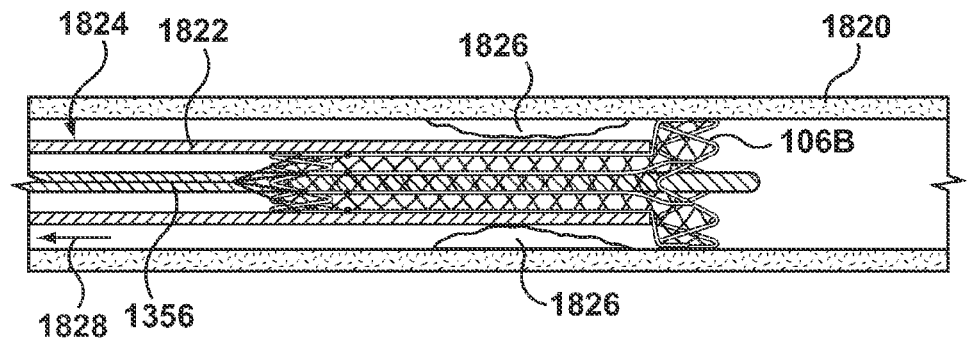
Figure 19C:
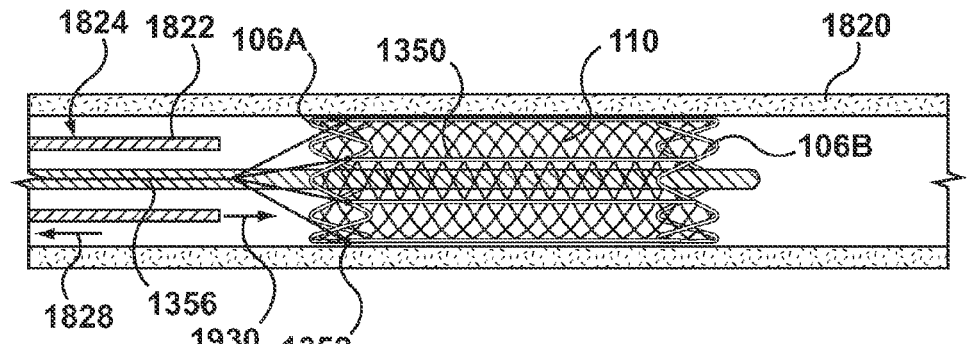

Once hybrid stent 1300 is in position at the treatment site within vessel 1820, sheath 1822 may be retracted or proximally withdrawn in the direction towards the operator as indicated by directional arrow 1828. Ring 106B of end portion 102B will self-expand and lodge against the vascular wall of vessel 1820 as shown in FIG. 19B as sheath 1822 is retracted thereover. With end portion 102B now anchored against the vascular wall of vessel 1820, sheath 1822 is further retracted or proximally withdrawn in the direction towards the operator as indicated by directional arrow 1828 while the operator simultaneously pushes a pusher or stopper distally in the direction away from the operator as indicated by directional arrow 1930 as shown in FIG. 19C. During this deployment step longitudinal compression bands 1850 may be held or maintained under tension such that proximal ring 106A of hybrid stent 1300 is essentially pushed in situ to connect bands 1350 thereto, thereby longitudinally compressing the stent and increasing the hoop strength thereof. Mechanisms for connecting bands 1350 to stent 1300 in situ include but are not limited to lodging stops 1352 into a slot as described with respect to FIG. 15 or pinching stops 1352 between a slot and a flap as described with respect to FIG. 16. With longitudinal compression bands 1350 attached to hybrid stent 1300, longitudinal compression bands 1350 continue to pull ends 102A, 102B toward each other and maintain and/or increase the hoop strength of longitudinally contracted body 104.

Figure 19D:
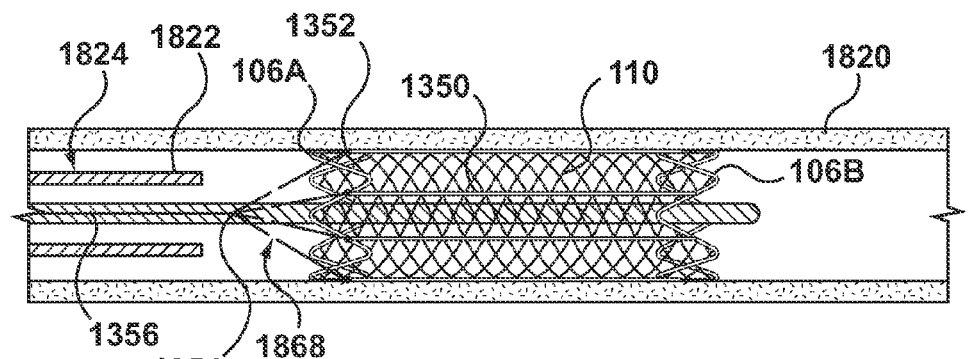

FIG. 19D illustrates hybrid stent 1300 fully deployed within vessel 1820, with longitudinal compression bands 1350 now coupled to both proximal and distal rings 106A, 106B of stent 1300. Longitudinal compression bands 1850 are now cut or otherwise broken apart as indicated by the gap shown at 1868 such that delivery catheter 1824 and pull string 1356 may be proximally retracted and withdrawn from the patient. As explained above with respect to FIG. 18C, mechanisms for disengaging longitudinal compression bands 1350 from pull string 1356 include an integral cutting element on delivery catheter 1824, utilizing a separate cutting element, utilizing an energy source to break apart longitudinal compression bands 1850, or forming weakened areas within longitudinal compression bands 1850 that break apart upon application of a sufficient pulling force by the user after stops 1352 are lodged within proximal ring 106A. After disengagement occurs, hybrid stent 1300 having longitudinal compression bands 1350 attached thereto for increased hoop strength may remain in situ.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A hybrid stent prosthesis comprising:
   a biodegradable tubular body having a proximal end and a distal end;
   a first non-biodegradable self-expanding ring coupled to the proximal end of the biodegradable body; and
   a second non-biodegradable self-expanding ring coupled to the distal end of the biodegradable body;
   wherein the hybrid stent includes protruding elements having a linear axis, the protruding elements only extend radially outward at an acute angle from at least an outer surface of the first and second rings away from a centerline of the stent transverse to the longitudinal axis of the stent, wherein the protruding elements are operable to lodge into tissue of a vessel wall to anchor the hybrid stent therein, and wherein the lodged protruding elements permit longitudinal contraction but prevent longitudinal expansion of the hybrid stent after deployment to increase the radial strength thereof.

2. The hybrid stent prosthesis of claim 1, wherein at least one of the protruding elements is a loop.

3. The hybrid stent prosthesis of claim 1, wherein the protruding elements radially extend from the hybrid stent at approximately forty-five degrees.

4. The hybrid stent prosthesis of claim 1, wherein the protruding elements are formed from a non-biodegradable material.

5. The hybrid stent prosthesis of claim 1, wherein protruding elements are also coupled to and extend radially outward from the biodegradable body.

6. The hybrid stent prosthesis of claim 1, wherein the biodegradable body is formed from one or more filaments having a pattern selected from braided, woven, wound, or knit.

7. The hybrid stent prosthesis of claim 1, wherein the biodegradable body is self-expanding.

8. The hybrid stent prosthesis of claim 1, wherein the biodegradable body is expandable via a user-applied compressive force applied after the second ring is deployed at a treatment site within a vessel.

9. The hybrid stent prosthesis of claim 1, wherein at least one of the protruding elements is a ball.

10. The hybrid stent prosthesis of claim 1, wherein at least one of the protruding elements is a rectangular arch.

11. The hybrid stent prosthesis of claim 1, wherein the protruding elements are in a staggered pattern along the surface of the first and second rings.

12. The hybrid stent prosthesis of claim 1, wherein the protruding elements are in a random pattern along the surface of the first and second rings.

13. A method of deploying a hybrid stent prosthesis at a treatment site within a vessel, the method comprising the steps of:
   threading a delivery catheter having the hybrid stent mounted at a distal end thereof through a vascular system until the hybrid stent is located adjacent to the treatment site, wherein the hybrid stent includes a biodegradable tubular body, a first non-biodegradable self-expanding ring coupled to a proximal end of the biodegradable body, and a second non-biodegradable self-expanding ring coupled to a distal end of the biodegradable body; and
   retracting a sheath of the delivery system to deploy the hybrid stent at the treatment site, wherein the hybrid stent is radially expanded and longitudinally compressed upon deployment,
   wherein the hybrid stent includes protruding elements having a linear axis, the protruding elements only extend radially outward at an acute angle from an outer surface of the hybrid stent away from a centerline of the hybrid stent transverse to the longitudinal axis of the hybrid stent, the protruding elements operable to lodge into tissue of a vessel wall to anchor the hybrid stent therein and permit longitudinal contraction but prevent longitudinal expansion of the hybrid stent after deployment to maintain the hybrid stent in the radially expanded and longitudinally compressed deployed configuration to increase the radial strength thereof.

14. The method of claim 13, wherein the biodegradable body is self-expanding and the step of retracting a sheath of the delivery system to deploy the hybrid stent includes retracting the sheath over the self-expanding biodegradable body.

15. The method of claim 13, wherein the step of retracting a sheath of the delivery system to deploy the hybrid stent includes retracting the sheath over the self-expanding second ring, and then further retracting the sheath over the biodegradable body while simultaneously applying a compressive force to the delivery system to radially expand and longitudinally compress the biodegradable body.

* * * * *